United States Patent [19]

Bornn

[11] Patent Number: 5,353,793
[45] Date of Patent: Oct. 11, 1994

[54] SENSOR APPARATUS

[75] Inventor: Robert Bornn, Los Altos, Calif.

[73] Assignee: Oishi-Kogyo Company, Tokyo, Japan

[21] Appl. No.: 797,538

[22] Filed: Nov. 25, 1991

[51] Int. Cl.$^5$ .............................................. A61B 5/04
[52] U.S. Cl. .................................. 128/642; 128/639; 128/644; 128/696; 607/152
[58] Field of Search ............... 128/695, 696, 644, 639; 607/148, 152

[56] References Cited

U.S. PATENT DOCUMENTS

| | | | |
|---|---|---|---|
| D. 278,746 | 5/1985 | Saynajakangas . | |
| D. 287,403 | 12/1986 | Kiiski et al. . | |
| D. 315,210 | 3/1991 | Rounds . | |
| 3,409,007 | 11/1968 | Fuller | 128/644 |
| 3,606,881 | 9/1971 | Woodson | 128/641 |
| 3,882,853 | 5/1975 | Gofman et al. | 128/641 |
| 3,989,036 | 11/1976 | Sasamori | 128/640 |
| 3,998,213 | 12/1976 | Price | 128/644 |
| 4,177,817 | 12/1979 | Bevilacqua . | |
| 4,365,634 | 12/1982 | Bare et al. . | |
| 4,381,012 | 4/1983 | Russek | 128/644 |
| 4,515,162 | 5/1985 | Yamamoto et al. | 128/640 |
| 4,763,660 | 8/1988 | Kroll et al. . | |
| 4,784,162 | 11/1988 | Ricks et al. . | |
| 4,889,131 | 12/1989 | Salem et al. . | |
| 4,909,260 | 3/1990 | Salem et al. . | |
| 4,911,169 | 3/1990 | Ferrari | 128/644 |
| 4,955,381 | 9/1990 | Way et al. . | |
| 4,966,154 | 10/1990 | Cooper et al. | 128/671 |
| 5,050,612 | 9/1991 | Matsumura . | |

FOREIGN PATENT DOCUMENTS

0339471 11/1989 European Pat. Off. .

OTHER PUBLICATIONS

American Health Products, Inc., Orange, Calif., "Monitron" product brochure, © 1987.
D. Stephen Robins, M.D., et al., Director, Communicore Research Consortium, Newport Beach, Calif., "Evaluation of a new, wireless, cardiorespiratory monitor", abstract.
Non-Invasive Monitoring Systems, Inc. (Nims), Miami Beach, Fla., "Respitrace Plus" and Respicardio Central product brochure.
Polar USA, Inc., Stamford, Conn., "Polar Heart Bra" product brochure chart, © 1988.
Baxter Healthcare Corporation, Chicago, Ill., "Dr. Marriott's Practical Placement" chart, © 1988.
Polar USA, Inc. electrode (marked Polar Electro Finland).

*Primary Examiner*—Lee S. Cohen
*Assistant Examiner*—Brian L. Caster
*Attorney, Agent, or Firm*—Gerald T. Sekimura

[57] ABSTRACT

A stretchable harness-like apparatus enables physiological parameters of a patient to be measured while he or she is ambulatory or stationary. The invention has a chest band, an optional shoulder band(s), and an optional abdominal band that can house respiration, pulse and ECG sensors. The shoulder band(s) are attached to the chest band and all of the bands are worn on the body under a low tension. The apparatus is typically used in conjunction with on-body monitoring electronics and radio-linked to remote alerting modules or it can be hard-wired to on-body or remote monitoring and alerting equipment. The compliant nature of the device allows for accurate monitoring without sacrificing patient mobility or comfort.

57 Claims, 7 Drawing Sheets

SENSOR APPARATUS

BACKGROUND OF THE INVENTION

1. Field of the Invention

The present invention relates to medical monitoring systems and, in particular, to a highly portable, non-invasive, simple to use, physiological sensor and sensor support apparatus. In addition to critical care monitoring, this apparatus can be utilized to comfortably and reliably monitor patients who are ambulatory or sleeping.

2. Discussion of the Prior Art

In the medical monitoring area, single and multi-channel electrocardiographic patient monitoring apparatus are currently available such as those manufactured by Hewlett-Packard Company of Palo Alto, Calif.; SpaceLabs of Redmond, Wash.; and Marquette Electronics of Milwaukee, Wis.

These types of systems require the patient's skin to be first vigorously scrubbed in preparation for gluing probes on or applying probes to the patient's skin with a "wet" process, or the systems use bulky apparatus to hold the probes in place. If these probes lose electrical contact with the patient's skin, trained personnel are needed to re-prepare the skin and re-attach the probes.

"Holter monitors" involve the use of a tape recorder to record signals from a number of "wet" electrode sensors which are hard-wired to the tape recorder. Uncomfortable sensors, wires, and equipment can dig into the patient's skin and restrict mobility.

Non-Invasive Monitoring Systems, Inc. (NIMS) of Miami Beach, Fla., manufactures a cardiorespiratory monitoring system called RESPITRACE PLUS which uses wet electrodes to monitor ECG and a pair of bands to measure respiration through inductance plethysmography. Inductance plethysmography, as implemented in the NIMS system, involves the use two bands. In each band, a wire is laid down in a sinusoidal pattern and sewn into a stretch fabric. An oscillator, having fragile connectors that tend to break readily, supplies a signal which is applied to the wire. As the signal propagates through the wire, changes in the shape of the wire caused by patient respiration, or other movement, cause changes in the signal out of the wire. Recent modifications to the NIMS product include the addition of one channel to measure ECG using traditionally attached electrodes. The bands used to measure respiration are not very durable and laundering the bands to sterilize them is difficult. Further, the wire-carrying band and oscillator create a bumpy surface which can cause discomfort to a patient when lying on them.

The monitoring apparatus manufactured by American Health Products of Orange, Calif. (see U.S. Pat. No. 4,889,131) and Polar U.S.A. of Stamford, Conn. eliminate the wet electrode because both include a belt worn around the torso of a patient, and hold sensors to monitor respiration and/or ECG signals. In the products of American Health Products, a sensor pair is used to measure multiple parameters. In the Polar products, a sensor pair is used to measure ECG only. Both belts have an elastic portion, but the portions of the belts that carry the sensors and electronics are "non-stretchable."

Polar has recently introduced a "Heart Bra" for use with its Heart Rate Monitors. The product is made of fabric and includes an elastic band to which two electrodes are mounted. It is believed that the elastic band has a loop which holds the electrode in a position between the elastic band and the user's skin, so that most of the electrode is in contact with the user's skin.

The American Health Products device uses impedance pneumography and houses the sensors in hard plastic modules that can be uncomfortable because they cannot conform to the patients body. None of the systems noted above are fully compliant or elastic and therefore can cause significant discomfort when worn.

Monitors which rely upon single band "impedance pneumography", such as the apnea monitor products manufactured by Healthdyne of Marietta, Ga., use artifact-prone electrodes. A single band system does not detect "obstructive apnea", a condition where the airway is obstructed and air is merely exchanged between the abdominal and thoracic cavities rather than replenished from the outside. Because these respiration sensors consist only of a chest band, the abdominal component of breathing is neglected.

With most of these monitoring systems, the major cause of false data, and thus false alarms, is artifact (signal noise). Artifact is typically generated by: patient activity; lead movement; rubbing of skin and clothing over leads or electrodes; or, in monitoring systems using radio telemetry, by electromagnetic interference (EMI). In the "stick on" or "wet" electrode systems the movement is caused by the electrode lead wires being pulled on thus causing the electrode to be separated from the patient's skin. It is frequently not obvious from a visual inspection of an electrode that it has come loose and an impedance check must then be performed to determine which electrode is loose. It is believed that in the band supported systems the movement of sensors relative to the patient's skin is contributed to by the non-elasticity of the support belt.

Therefore, with existing systems, the patient's mobility is typically intentionally limited to reduce artifact. Further, the physical constraints of the apparatus also operate to limit the patient's mobility. It is also believed that none of the prior art allows practical monitoring of an ambulatory patient over an extended period of time.

SUMMARY OF THE INVENTION

The restrictions on mobility and comfort imposed by the prior art, as well as other associated problems, are overcome by the present invention. The present invention allows monitoring of physiological parameters of an ambulatory patient, while utilizing techniques that minimize artifact and its affect on accurate, cost-effective, critical-care monitoring.

The present invention is a harness-like apparatus, worn by a patient, that positions sensing means firmly yet comfortably on the patient. In the preferred embodiments, the apparatus includes a chest band, at least one shoulder band, and an optional abdominal band. Both ends of the shoulder band are connected to the chest band, one in the front and the other in the back.

For comfort and mobility, the bands are made from a soft, resilient material. This resilience allows for the reduction of artifact, as explained below. The resilience of the material also allows the bands to stretch as the patient breaths and moves. Polyurethane is the material used in the preferred embodiment because it has a modulus of elasticity close to that of skin, it is moisture and static resistant, and polyurethane can be sterilized with an alcohol wipe.

Sensor means are located at various locations inside the bands and on the outside of the bands contacting the patient's skin. Typical sensors used in this apparatus can be ECG electrodes, piezoelectric sensors for monitoring respiration and pulse, skin and axilla temperature sensors, and activity or position sensors.

A major source of artifact comes from movement of sensors relative to the patient's skin. This movement is reduced by wearing the resilient bands under tension (4 to 16 ounces, for example). Because the entire length of the bands stretch in the present invention, as opposed to the non-elastic regions which accommodate the sensors in the prior art, all of the sensors can be kept from moving away from the skin as the patient's body moves. The complete elasticity of the present band is also much less restricting on the patient's movements than a belt which includes non-elastic sections.

The proper tension can be achieved in the bands by sizing a one piece sensor apparatus to fit a particular size range of patients, or by having adjustable fasteners connecting the various segments of the apparatus together. In the preferred embodiment a hook and loop type fastener is employed to connect the two ends of the chest band together under one arm, and to attach one end of each shoulder band to the chest band in the back.

The apparatus of the invention has many sensor locations in the chest, shoulder, and abdominal bands as opposed to relatively few sensors found in typical real-time critical care cardiac monitors. Although stress test or treadmill type devices utilize many sensors, they are not meant for long term monitoring, require extensive skin preparation, and are hard-wired thereby preventing ambulatory monitoring. The multiplicity of sensors in the present invention allows for the reduction of artifact in two ways. First, monitoring equipment used with this apparatus can utilize the redundant sensors to cross check for the presence of a valid "QRS" signature (wave shape of heart beat) on one or more channels before signalling an alert. This decreases false alarms. Second, the system can scan all of the channels looking for the best signal. Depending on the orientation of the sensors on the patient's body at the time, some sensors may provide more useful signals than others.

The present invention employs wiring means to connect the sensors to monitoring equipment. This connection can be a direct one from the sensing apparatus through a connector to the external equipment. The connection can also be accomplished by coupling the sensors with an on-patient processor and/or radio telemetry unit which communicates with external monitoring equipment. In the later case, the patient-mounted equipment can be supported comfortably by the apparatus of the present invention. A radio link between the sensor apparatus and the monitoring equipment can significantly reduce the artifact that exists with a completely hard-wired system, and of course, can greatly increase mobility.

The wiring means run from the sensors, and in most cases through the chest, shoulder, and abdominal bands. Therefore, the wiring means should be capable of elongating with the bands to avoid restricting the patient and interfering with the proper operation of the sensors. The apparatus of the present invention accomplishes this wiring means elongation in one of several ways. The conductors can be snaked through the bands in a series of "S" loops that straighten as the bands stretch. The conductors can also be woven in a mesh that is capable of elongating. Alternatively, the conductors can be printed on the skins of the bands. The conductors can be printed in a zig-zag pattern or the bands can have a corrugated surface that flattens out as the band elongates. In all three of these cases, the wiring means are placed in the bands in a manner which minimizes bulk to allow the patient to lie on the bands comfortably.

In addition to the sensors, wiring means, and possible processors and telemetry equipment previously mentioned, it is envisioned that the apparatus of the present invention can also support devices for communicating with the patient and batteries for powering the on-board equipment. Communication devices could include: annunciators using audible tones and/or tactile signalling and/or digitized voice messages for warning the patient of problems and/or providing the patient with instructions; signalling means to allow the patient to request help or to cancel an alarm; and a speaker and microphone arrangement that would allow the patient or someone assisting the patient (e.g. giving the patient cardiopulmonary resuscitation) to communicate with a care giver or emergency personnel. These additional devices provide a greater control over false alarms, more security, and increased privacy and sense of dignity for the patient by involving him or her in the monitoring process.

These aspects and other features and advantages of the present invention will become more apparent from a perusal of the following specification taken in conjunction with the accompanying drawings wherein similar characters of references refer to similar elements in each of the several views.

DESCRIPTION OF THE PREFERRED EMBODIMENT

Figure 1A:
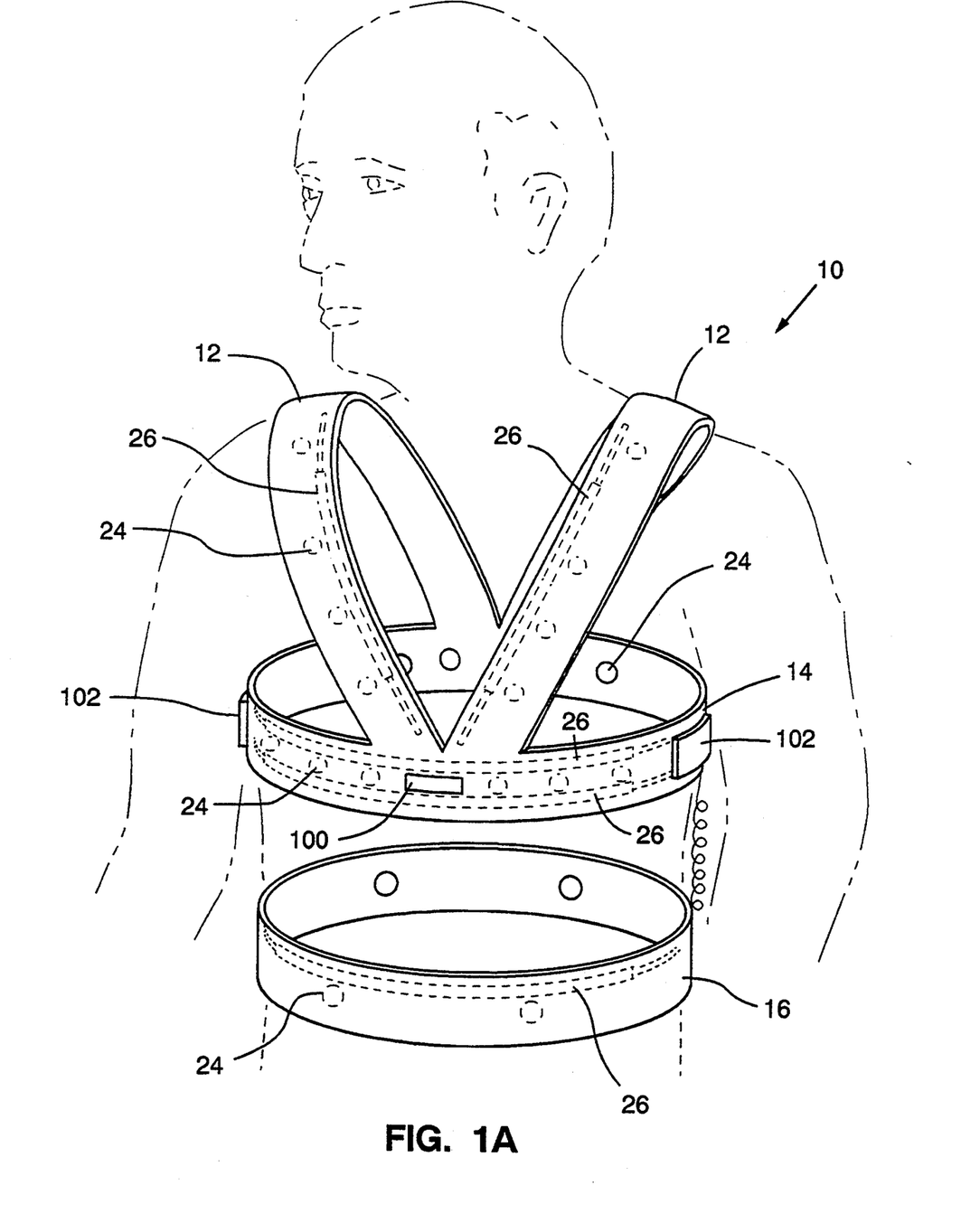
FIG. 1A is a frontal perspective view of a one piece embodiment of the chest and shoulder bands, and the abdominal band as worn by a patient.

Referring now to FIG. 1A, the sensor assembly of the preferred embodiment includes a chest band 14 which is worn high around a patient's rib cage just below the breasts. A pair of shoulder bands 12 each have an end attached to the back portion of the chest band 14 and the opposite end attached to the front portion of the chest band 12. An optional abdominal band 16 is worn around the patient's abdomen above the hips and below the waist. The abdominal band is electrically connected to the chest band by a self-coiling cable that plugs into the chest band under one arm. The material used for the chest, shoulder and abdominal bands in the preferred embodiment is Akton, a visco-elastic polymer, manufactured by Action Products, Inc. of Hagerstown, Md. Akton is a proprietary type of polyurethane having a gel-like core surrounded by a skin. Akton 100 series is used for the gel and Akton PT 9300 series is used for the outer film or skin. For comfort, a 3 mm thick skin is used for the side of the bands that contact the patient, and for durability an 8 mm thick skin is used for the side of the bands that face away from the patient. The bands currently being used are half an inch thick and two inches wide, however, smaller thicknesses and widths are envisioned to provide a more lightweight structure. For example, thicknesses such as $\frac{1}{4}''$ and $\frac{3}{8}''$ and widths of 1" and 1½ are being considered.

The chest, shoulder, and abdominal bands are all adapted to support physiological data sensors. The two primary types of sensors utilized in the present invention are ECG electrodes 24 and tensioned sensors 26. In the preferred embodiment, the tensioned sensors are piezoelectric sensors. Depending upon their placement relative to the heart, blood vessels, arteries, or the lungs, these tensioned sensors 26 are capable of sensing respiration or pulse signals. Their respective signal outputs are passed through different processing filters (not part of the present invention) to obtain the appropriate data from each type.

Figure 1B:
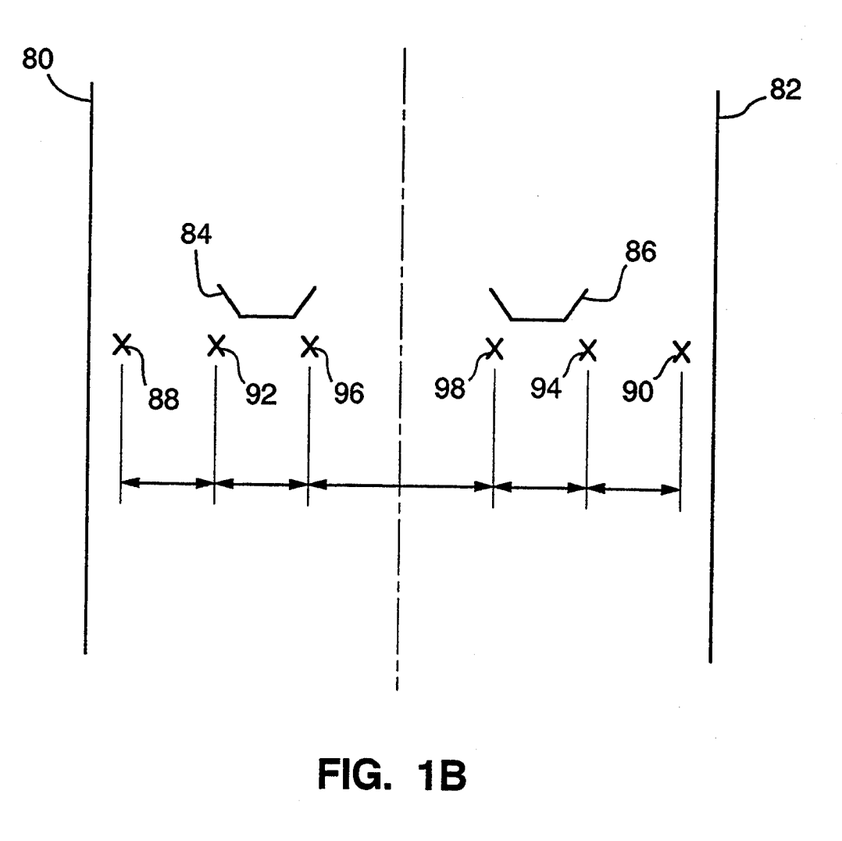
Figure 1B is a schematic representation of the positions of the ECG sensors on the front portion of the chest band.

A minimum of seven ECG sensors 24 are used in the present invention. One is used as a reference and the other six form three pairs of sensors. They can be configured in a number of different ways, but they are generally configured around the heart and evenly spaced through the bands. The preferred embodiment uses a total of eighteen ECG sensors 24, four in the front portion of each shoulder band 12, six in the front portion of the chest band 14, and four in the back portion of the chest band 14. Preferably, the sensors 24 are positioned by band 14 on the patient's body as shown in FIG. 1B. The patient's body is shown in abstract with lines 80 and 82 indicating the arm axes of the right and left arms, respectively. Symbols 84 and 86 indicate the right and left breasts, respectively. The preferred positions are as follows. Positions 88 and 90 are just to the front of the right and left arm-axes, respectively. Positions 92 and 94 are just under the arm side of each of the breasts 84 and 86. Positions 96 and 98 are under each breast 84 and 86 toward the center of the body. Preferably, sensors 96 and 98 are spaced four inches apart, while the spacing between sensors 96 and 92, sensors 92 and 88, sensors 98 and 94, and sensors 94 and 90, is two inches. Distances shown are circumferential distances.

The preferred embodiment also has at least two piezoelectric sensors 26 located across the front portion of the chest band 14. Optionally a third piezo is located in the abdominal band 16 and fourth and fifth sensors are located across the front portion of each shoulder band 12. The approximate positioning of these sensors is indicated in FIG. 1.

The two piezoelectric sensors 26 in the shoulder bands 12 are used to sense the patient's pulse, and the two in the chest band are used to sense pulse and respiration. The piezo sensor in the abdominal band 16 is used to detect respiration. Having sensors 26 for detecting respiration both on the abdomen and on the chest enables monitoring equipment to distinguish between normal mechanisms of breathing (chest and abdomen moving together in phase) and obstructive or paradoxical breathing (chest and abdomen moving out of phase).

The length of the respiration sensors should be long enough to prevent occlusion, which occurs when the patients weight is resting on the entire piezoelectric element. If a sensor is short enough to allow occlusion, respiration signals may not be produced by the sensor. The piezoelectric elements in the chest band are sized to accommodate the chest size of the patient (under the breast). For example, for a patient chest size of 40 inches, the piezo element has a length of approximately 15 inches.

Figure 2A:
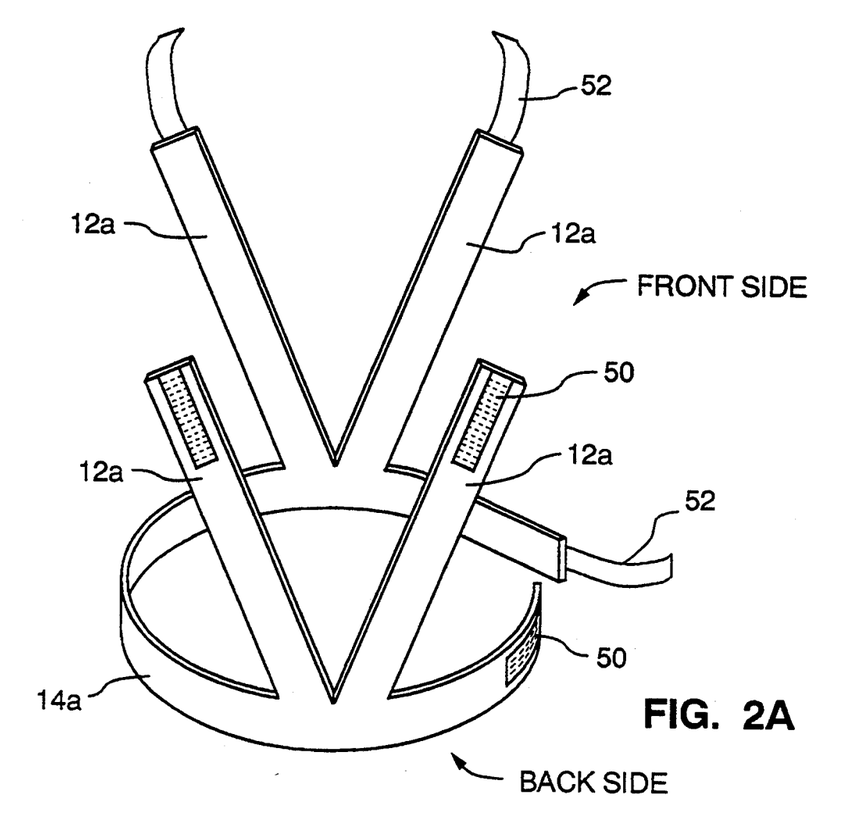
FIGS. 2A and 2B are rear views representing two examples of fastening and adjusting means of the chest and shoulder bands.
Figure 2B:
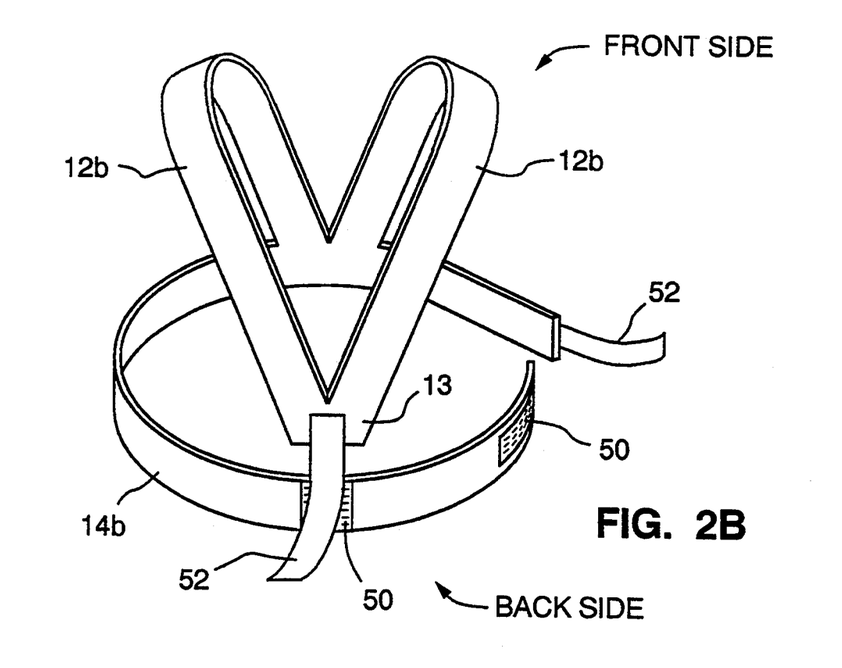

FIGS. 2A and 2B show alternatives to the one piece construction illustrated in FIG. 1. In FIG. 2A the front and rear portions of the shoulder bands 12a are separated and can be adjusted and fastened at the top of the patient's shoulders. The front and rear portions of the chest band 14a are attached on one side and separated on the other side and can be adjusted and fastened under one arm of the patient. In the preferred embodiment a hook and loop arrangement, 52 and 50 respectively, such as Velcro ® is utilized at each fastening point. The optional abdominal band (not shown) is adjustably fastened in the same manner as the chest band 14a. FIG. 2B shows a similar fastening arrangement having the shoulder bands 12b attached to the chest band 14b in the front and attached to each other in the back. The common end 13 of the shoulder bands 12b is adjustably fastened to the back portion of the chest band 14b with a hook and loop arrangement, 52 and 50 respectively.

Whether the bands are of a one piece construction or adjustably fastened, they are worn under a tension (preferably 4 to 16 ounces, and optimally 12 ounces) to ensure proper operation of the sensors. It is an important aspect of the present invention that the material used in the bands 12, 14, and 16, is resilient and self tensioning, and has a consistency which cushions the patient from the contours of the physiological sensors, the interconnecting cabling, and any on-board connectors and processing/telemetry modules, and which also cushions the physiological sensors to stabilize the physiological sensors relative to the patient's skin. The self-tensioning property plays an important role in maintaining the physiological sensors in contact with the patient's skin without the need for "wet" electrodes or high-tack adhesives. The resilient and cushioning property of the material promotes patient comfort as well as reduces artifact due to movement of the patient or movement of the sensors relative to the patient.

Figure 3A:
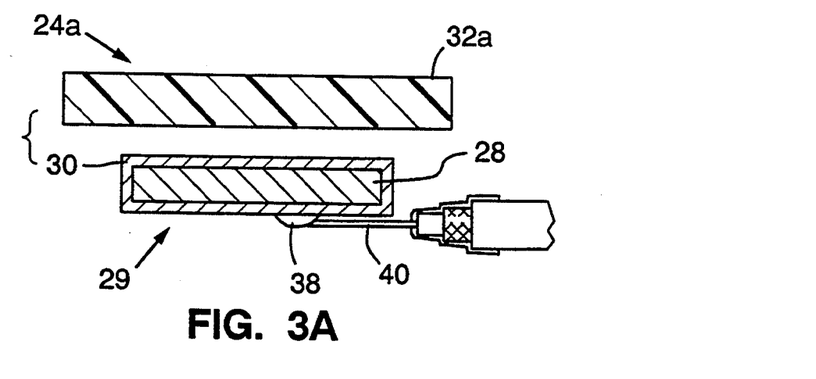
FIGS. 3A, 3B and 3C are side elevational exploded cross-sectional views of various sensor electrode embodiments.
Figure 3B:
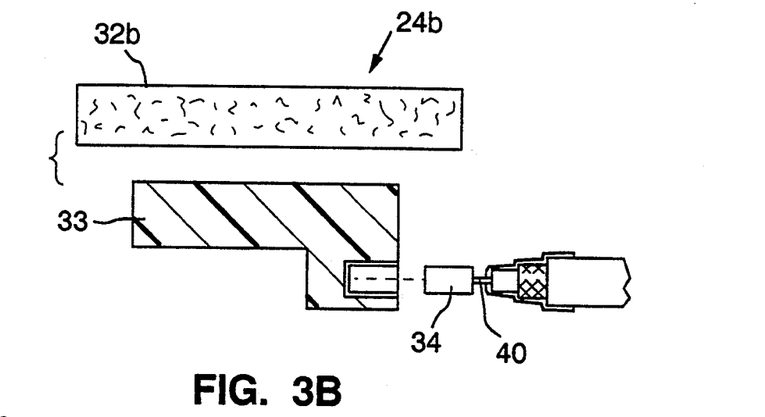

Various constructions and features of ECG electrodes 24 are shown in FIGS. 3A through 3D in exploded view. FIGS. 3A and 3B show a conductive plating 30 over a metallic substrate 28. The center conductor 40 of a coaxial cable is soldered 38 on one side of the plated substrate 29 while the outer shield of the cable is unterminated and covered with an insulated covering such as shrink tubing. A compliant conductive pad 32a is attached to the opposite side of the plated substrate 29.

To be able to transmit a good ECG signal, the free side of pads 32a, 32b, or 32c, should be able to tenaciously work through any hair and perspiration on a patient's skin and remain slightly tacky against the skin. Striations 36, as shown in FIG. 3D, or other texture, on the free side of pads 32a, 32b, or 32c, help to achieve this goal. A diamond shaped or pebbled surface is able to slightly roughen up the skin as it is pressed against it, and also provides channels for allowing perspiration to flow away when the electrode is compressed against the skin. When an adhesive is used to enhance contact between the sensor 24 and the patient's skin, it should be selected to provide a "mild" adhesion. The adhesive is preferably a "low aggressive" type.

In the preferred embodiment the conductive pad 32 (FIG. 4C) is a 1/16 inch thick by two inch long oval made of carbonized rubber 32a or Promeon® brand hydrogel 32b. Promeon hydrogel made by Medtronics, Inc. of Minneapolis, Minn. In an alternative embodiment, FIG. 3A, this pad 32 can be placed over the plated substrate 29. The substrate 29 has a conductive plating 30 of 10 to 20 microns of gold and a metallic substrate 28 of copper, and is about one inch in diameter and 10–15 mils. thick. The materials used for the plating 30 and the substrate 28 may be changed or the plating may be omitted, but the materials used should be conductive, resist corrosion, and not enable electrolytic action.

Figure 3C:
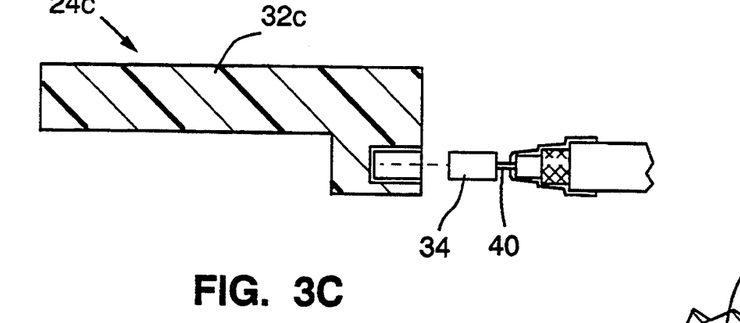
Figure 3D:
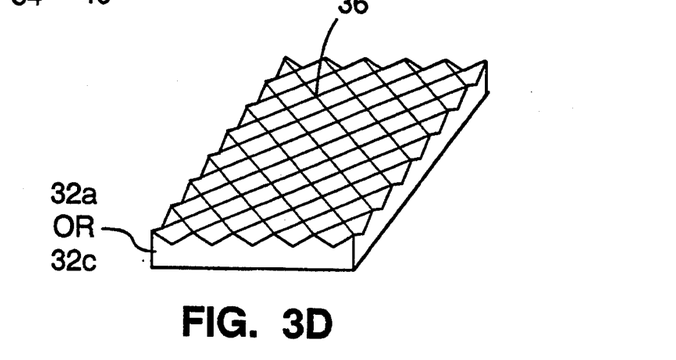
FIG. 3D is an isometric view of the top striated surface in one embodiment of a sensor electrode.

FIGS. 3B and 3C illustrate preferred embodiments of the ECG electrodes. These embodiments do not use a plated substrate. Instead, a conductive substrate 32c of carbonized rubber is used. The conductive substrate 32c can be used directly in contact with the patient's skin, as shown in FIG. 3C, where the contacting surface is suitably textured. Alternatively, as shown in FIG. 3B, a Promeon pad 32b, can be placed over the conductive substrate 33 to provide the appropriate interface with the patient's skin. The center conductor 40 of the coaxial cable can be fitted with a connector that engages a mating connector which is molded into the carbonized rubber pad 32c as shown in FIG. 3C. In this arrangement, the carbonized rubber pad 32c can have a suitably textured surface to contact the patient's skin directly, or a Promeon pad 32b may be placed over the rubber pad 33 for contact with the skin. The rubber pad 33 in this case would be an inch or smaller in diameter. See FIG. 3B.

Figure 4A:
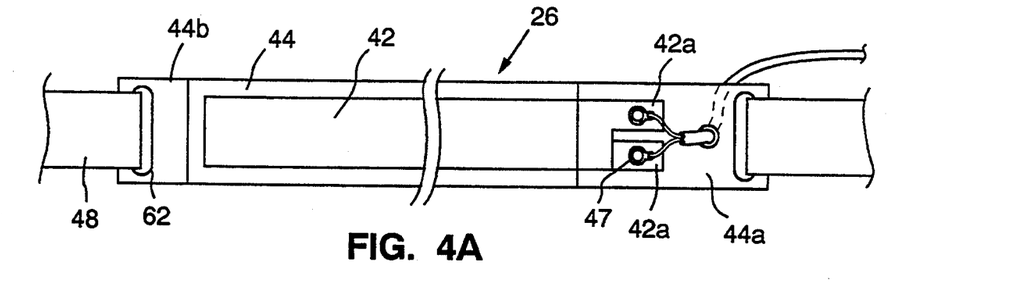
FIG. 4A is a fractional elevational view of a piezoelectric sensor and portions of its connecting straps.
Figure 4B:
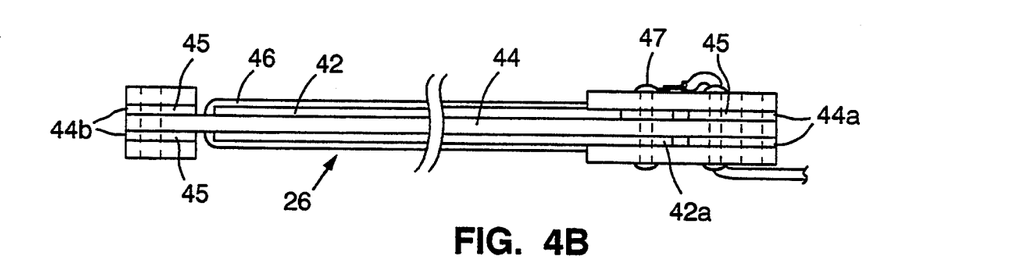
FIG. 4B is an enlarged cross-sectional view of the piezoelectric sensor shown FIG. 4A taken along line 4B—4B in the direction of the arrows.
Figure 4C:
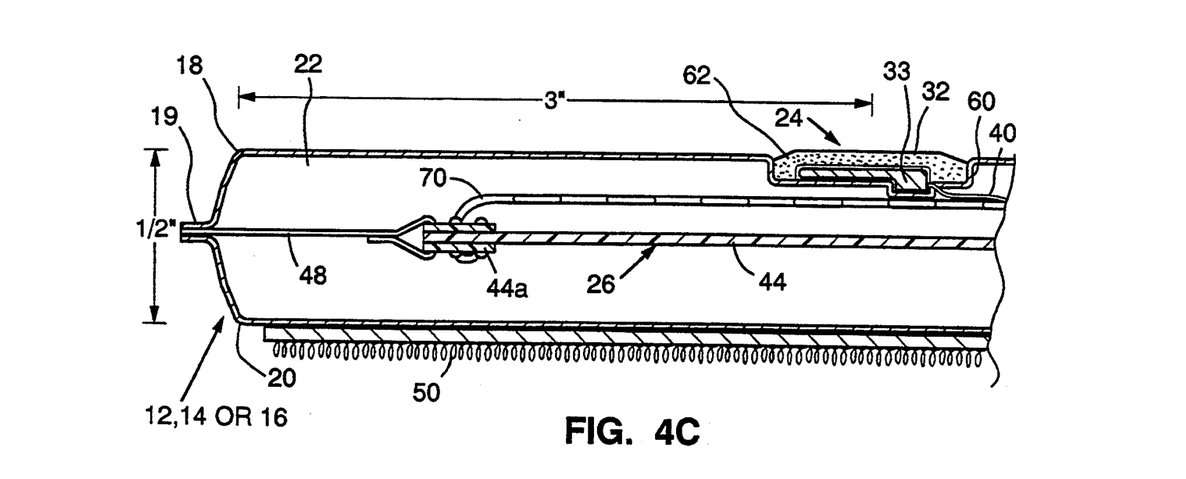
FIG. 4C is an enlarged longitudinal cross-sectional view of an end portion of a shoulder, chest or abdominal band taken along the centerline of a piezoelectric sensor.

Referring now to FIG. 4C, recesses 60 are vacuum formed in the inner skin 18 and gel 22 of the band 12, 14 or 16 to house the ECG sensor assemblies 24. Conductors 40 from disk 28 pass through the skin 18 at the bottom of the recess 60. The disk 28 is attached to the bottom of the recess with medical grade adhesive. The conductive pad 32 is then placed over the disk 28 and the pad's edges 62 are attached to the bottom of the recess 60 with more adhesive, leaving the center of the pad 32 slightly higher than the surrounding skin 18 of the band to ensure good contact with the patient's skin. Because the disk 28 is smaller in diameter than the pad 32 and the recess 60, the pad's edges 62 lie slightly below the surface of the skin 18 to resist peeling away from the bottom of the recess 60.

FIGS. 4A and 4B show elements of a piezoelectric respiration or pulse sensor 26, such as a sensor manufactured by ATOCHEM of Valley Forge, Pa. A piezoelectric film 42 such as of Kynar ® about 110 microns thick is applied to both sides of a four mil thick strip of Mylar ® 44 which is about one half inch wide and 15 inches long, leaving about an inch from both ends of the Mylar ® 44 and a sixteenth of an inch from both edges uncoated. Non-overlapping, tab-like projections 42a of the film 42 are made on opposite sides of the Mylar ® strip 44 to serve as connection points for wires. Short pieces of five mil thick Mylar ® 44a, 44b are attached with one half mil thick adhesive 45 to both sides of both ends of the long Mylar ® strip 44 to act as strain reliefs for the Mylar ®. Slots 62 are cut in both ends of the sensor 26 to allow elastic bands 48, such as of Akton, to attach to the sensor 26. Eyelets 47 are inserted through the assembly to provide connection from the wires to the piezoelectric film 42. Suitable clearance holes (not shown) should be provided in the small strips of Mylar ®44a to allow one head of each rivet 47 to fully contact the film 42. A third eyelet near the first two can be used as a strain relief for the wiring. The entire assembly is covered with a conformal coating 46 to insulate the piezoelectric film 42 and prevent corrosion. The free ends of the elastic bands 48 are bonded between the ends 19 of the inside 18 and outside 20 skins of the front portion of the chest, shoulder, and abdominal bands 12, 14 and 16, respectively, to place the sensor assemblies 26 under a slight pretension inside the bands, as shown in FIG. 4C.

Figures 5A, 5B:
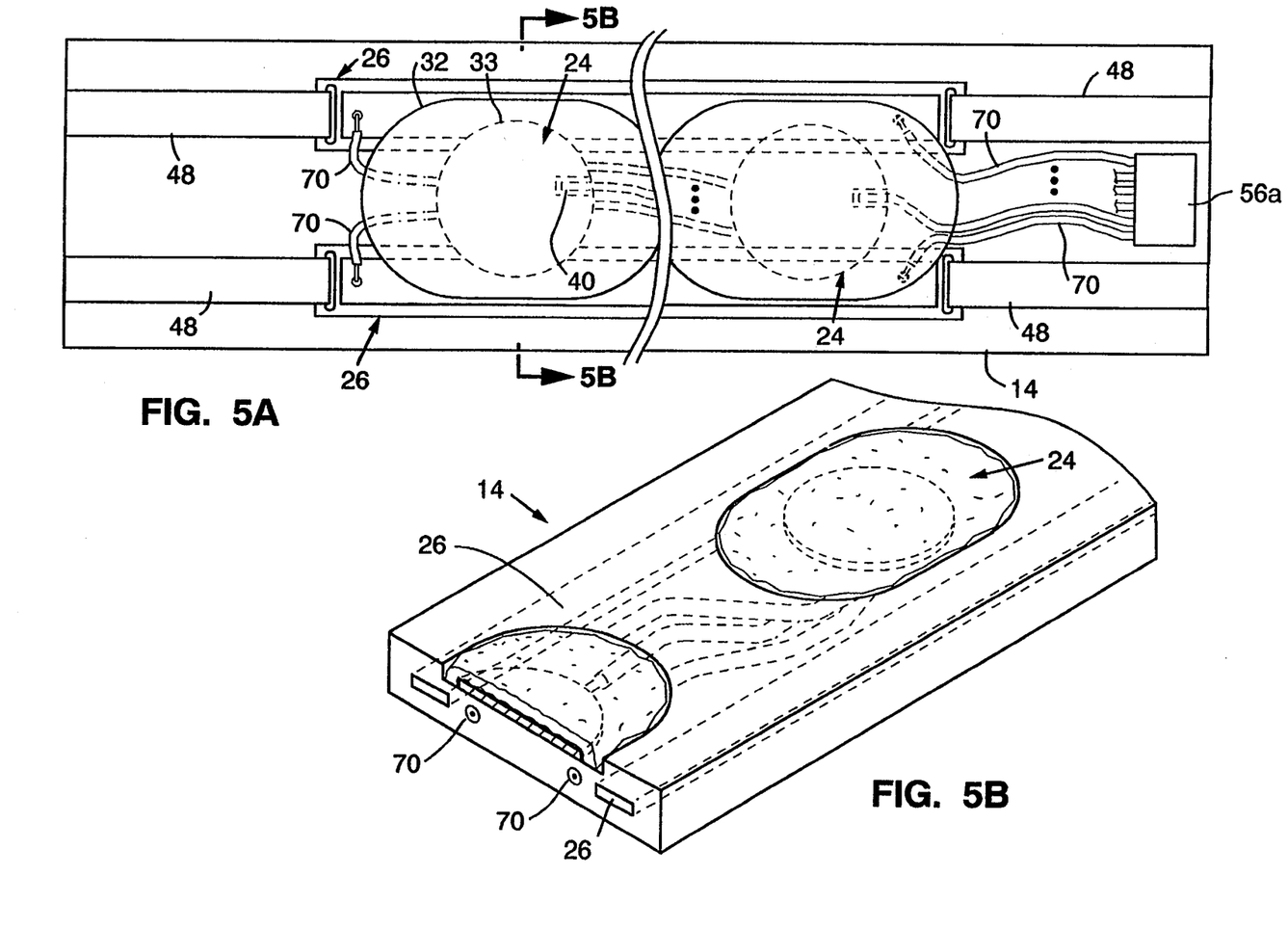
FIG. 5A is a fractional elevational view showing the interior of the front half of the chest band.
FIG. 5B is a fractional cross sectional isometric view of the chest band shown in FIG. 5A taken along line 5B—5B in the direction of the arrows.

FIGS. 5A and 5B further show the positioning of sensors 24 and 26 in the front portion of the chest band 14 and illustrate how cables 70 are routed from a connector 56a to these sensors through the band. In this embodiment the cables are snaked through the interior gel of the band in a repeated "S" fashion to allow the cables to elongate when the band is stretched. The cables should be one third longer than the portion of band that they are in. The prototype of the invention uses a multi-conductor connector 56a, model number 3564, manufactured by 3M of Minneapolis, Minn., however, it is envisioned that a miniaturized version of this connector will be used in commercial embodiments of the invention.

Figures 6A, 6B:
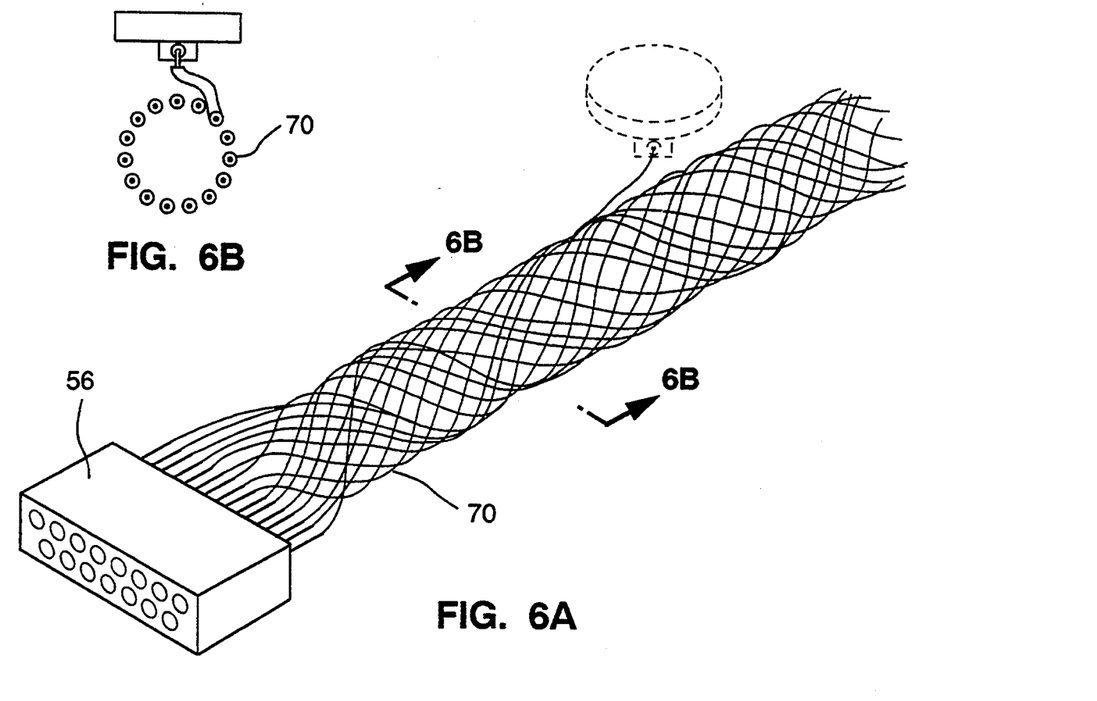
FIG. 6A is an isometric view of an elongatable woven set of conductors.
FIG. 6B is a cross sectional view of the conductors shown in FIG. 6A taken along line 6B—6B in the direction of the arrows.
Figure 7:
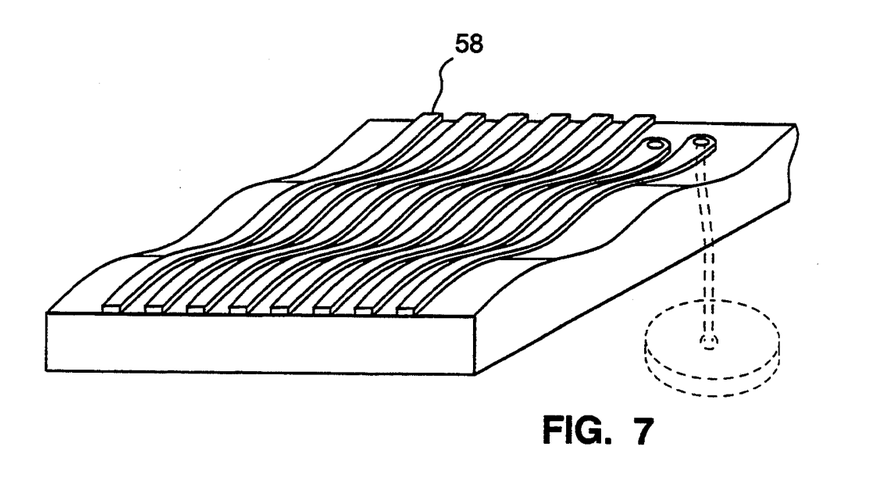
FIG. 7 is an isometric view of a section of band containing elongatable conductor traces on its surface.

In an alternate embodiment shown in FIG. 6A, the cables are woven in a mesh-like tube that can elongate. In yet another embodiment shown in FIG. 7, it is envisioned that the conductors can be printed onto the surface of the bands, or traces can be encapsulated in the surface of the bands. The conductors would be formed in a zig-zag pattern or the surface would have corrugations that flatten out as the bands are stretched. Preferably the cables 70 are shielded coaxial cables. It has been found that the shielding causes an appreciable reduction in noise. Preferably, for each cable, only one end of the shield is grounded.

Other features provided by the present invention can include a manually operated switch 100 positioned in band 14 where shoulder bands 12 join band 14. The manually operated switch 100 can be a membrane switch positioned in the band 14 so that it will be actuated only if squeezed in a direction along the width of the band 14. This prevents the switch from being falsely enabled by bed clothes or buttons being pushed up against it. In the preferred placement of the switch 100, it will be activated when the patient grabs the band 14 in the vicinity of the switch and squeezes it. Alternatively, the switch can be located on the chest band 14 under one arm.

It is also to be noted that the placement of the sensors 24 and 26 in bands 14 is such that the area of the bands worn beneath the axilla of the patient are available to house processing and telemetry modules 102. It is envisioned that where direct wiring of the sensors to external equipment is not desireable, processing of the signals can be performed by an on-board processing module positioned in a cushioned pocket in band 14 located under an arm of the patient. A telemetry module, located in another cushioned pocket in band 14 under the other arm of the patient would then be used to transmit the processed information and/or raw data to a transceiver station. The telemetry will have a bi-directional link permitting remote commands to initiate the transmission of data to the transceiver station.

As can be appreciated from the preceding description, the present invention provides at least three mechanisms which operate to maintain the ECG sensors in contact with the skin of the patient: tension, texture, and tack. Tension is provided by the compliant, resilient nature of the chest band or abdominal band. As discussed above, when the band of the present invention is worn around the patient's chest or abdomen, this places the band under tension. This tension serves to urge the ECG sensors into contact with the patient's skin, and to return the ECG sensor into contact with the skin after being separated from the skin by a temporary pulling on the band. It has been found that tension in the range of 4 to 16 ounces provides the appropriate amount of biasing for the sensor and comfort level to the patient.

The texture of the ECG sensor-to-skin interface provides a frictional component that resists side-to-side movement.

The degree of adhesion or "tack" used in the ECG sensor-to-skin interface provides a frictional component, and also provides some resistance to lifting forces on the sensor.

In accordance with the present invention, the combinations of levels of tension, texture, and tack should be selected according to the body type of the patient. For example, for a large, active patient, a high level of texture should be used, with a light level of tack. This is because with a large, active patient, it is likely that significant perspiration will be present. A textured interface will slightly abrade the skin to improve contact, and will permit perspiration to flow away from the sensor while maintaining sensor contact with the skin. The tension used can be at the upper end of the range since more physical activity can be expected. (For patients where excessive perspiration might be a problem, a outer covering can be used on the bands to wick away moisture.)

On the other hand, for patients of slight build with delicate and/or dry skin, the texture used should be light and the tack used should be heavier. The skin of such patients will tend to be drier and less conductive. Thus a textured interface will not be as effective as a "tacky" interface. Further, a textured interface will probably be more irritating to delicate skin. The tension used should be at the lower end of the range.

Beyond the use of texture, tack and tension to support the ECG sensors, the shoulder bands described above can be used to provide support for the chest band, in addition to carrying their own piezo and ECG sensors.

The terms and expressions which have been employed here are used as terms of description and not of limitation, and there is no intention, in the use of such terms and expressions, of excluding equivalents of the features shown and described, or portions thereof, it being recognized that various modifications are possible within the scope of the invention claimed.

What is claimed is:

1. A sensor support apparatus, suitable for wearing by a patient, comprising:

chest band means for forming a compliant loop having a selected circumference such that when said chest band means is worn around the patient's chest, substantially all of said chest band means elongates and produces a resilient tension, said chest band means formed of a gel-like core, and having a front portion and a back portion;

shoulder band means for forming a compliant band having a first end connected to the back portion of said chest band means and a second end connected to the front portion of said chest band means, said shoulder band means having a selected length and being formed of a gel-like core, such that when said shoulder band means is worn over the patient's shoulder and said chest band means is worn around the patient's chest substantially all of said shoulder band means elongates and produces a resilient tension; and a plurality of sensor means for sensing at least one physiological parameter of the patient, wherein said sensor means are positioned on said chest and shoulder band means, and further wherein resilient tensioning provided by said chest and shoulder band means operates to maintain the sensor means in proper physical orientation with respect to the patient's body for proper operation.

2. The apparatus of claim 1, wherein said chest band means and said shoulder band means are each comprised of an outer skin formed of and filled with a visco-elastic polymer.

3. The apparatus of claim 2, wherein said visco-elastic polymer is a polyurethane.

4. The apparatus of claim 2, wherein said chest and shoulder band means further contain recesses in said outer skin which extend into said visco-elastic polymer for housing said sensor means.

5. The apparatus of claim 4 wherein each of said recesses have a bottom of predetermined width and side walls, and each of said sensor means comprise a conductive substrate fastened to said recess bottom and having a width less than said predetermined width of said recess bottom;

interface means communicating with the conductive substrate for forming a conductive and galvanically inert interface between the conductive substrate and the patient's skin.

6. The apparatus of claim 5, wherein said interface means substantially fills the recess.

7. The apparatus of claim 1, wherein said chest band means comprises a length of an outer skin formed of and filled with a visco-elastic polymer and having first and second ends; and fastening means for removably connecting the first end of said outer skin to the second end.

8. The apparatus of claim 7, wherein said fastening means is adjustable.

9. The apparatus of claim 1, wherein said chest band means is formed of a continuous loop of an outer skin formed of and filled with a visco-elastic polymer.

10. The apparatus of claim 1, wherein one of the first and second ends of said shoulder band means is removably connected to said chest band means.

11. The apparatus of claim 10, wherein said fastening means is adjustable.

12. The apparatus of claim 1, wherein said sensor means comprise means for sensing ECG signals.

13. The apparatus of claim 12, wherein said ECG sensor means comprise:
a conductive substrate;
a thin layer of a conductive, galvanically inert substance enveloping said substrate; and
means affixed to said thin layer for forming a conductive and inert interface between said ECG sensor means and the patient's skin.

14. The apparatus of claim 13, wherein said interface forming means include a hydrogel.

15. The apparatus of claim 14, wherein said interface forming means include a striated surface.

16. The apparatus of claim 13, wherein said interface forming means include
a layer of carbonized rubber affixed to said thin layer.

17. The apparatus of claim 16, wherein said interface forming means include a striated surface.

18. The apparatus of claim 13, wherein said shoulder and chest band means each have a surface which comes in contact with the patient's skin, said surfaces further have recesses for housing said ECG sensor means, and said sensor means are adhesively attached to bottom of said recesses and are generally flush with said surfaces.

19. The apparatus of claim 12, wherein said ECG sensor each comprise a layer of carbonized rubber.

20. The apparatus of claim 1, wherein said sensor means comprise means for sensing changes in the tension in said chest band means.

21. The apparatus of claim 20, wherein said means for sensing changes in tension comprise a strip of piezoelectric material positioned longitudinally in said chest band means.

22. The apparatus of claim 1, wherein said sensor means comprise means for sensing changes in the tension in said shoulder band means.

23. The apparatus of claim 1, wherein said sensor means comprise a strip of piezoelectric material positioned longitudinally in said chest band means for sensing small amounts of flexing caused by the patient's pulse.

24. The apparatus of claim 1, wherein said sensor means comprise a strip of piezoelectric material positioned longitudinally in said shoulder band means for sensing small amounts of flexing caused by the patient's pulse.

25. The apparatus of claim 1, further including wiring means for providing electrical connection to said sensor means, said wiring means being formed in a manner which permits said wiring means to elongate when said chest band means and shoulder band means are placed under tension.

26. The apparatus of claim 25, wherein said wiring means are embedded within a visco-elastic polymer located in said chest and shoulder band means, and out of contact with the patient's skin.

27. The apparatus of claim 26, wherein said wiring means are snaked in an accordion fashion through the visco-elastic polymer to permit stretching of said chest and shoulder band means.

28. The apparatus of claim 26, wherein said wiring means include a plurality of conductors which are woven together to form a structure that elongates when said chest and shoulder band means elongate.

29. The apparatus of claim 25, wherein said wiring means are formed on a skin of said chest band means and said shoulder band means in a manner which permits said wiring means to elongate when said chest band means and shoulder band means are placed under tension.

30. The apparatus of claim 1, further including a patient-activated switch positioned in the chest band means.

31. The apparatus of claim 30, wherein the switch is located in the center of the front portion of the chest band means.

32. The apparatus of claim 30, wherein the switch is located in the chest band means such that said switch is positioned under an arm of the patient.

33. A sensor band, suitable for wearing by a patient, comprising:
torso band means formed of a gel-like core, for forming a compliant loop having a selected circumference such that when said torso band means is worn around the patient's torso substantially all of said torso band means elongates and is placed under a resilient tension; and
sensor means for sensing at least one physiological parameter of the patient, wherein said sensor means are positioned on and cushioned by said torso band means, and further wherein the resilient tension of said torso band means operates to maintain the sensor means in proper physical orientation with respect to the patient's body for proper operation.

34. The apparatus of claim 33, wherein said sensor means include a strip of piezoelectric material positioned longitudinally in said torso band means.

35. The apparatus of claim 33, wherein said torso band means are comprised of an outer skin formed of and filled with a visco-elastic polymer.

36. The apparatus of claim 35, wherein said visco-elastic polymer is a polyurethane.

37. The apparatus of claim 35, wherein said torso band means further contain recesses in said outer skin which extend into said visco-elastic polymer for housing said sensor means.

38. The apparatus of claim 37, wherein each of said recesses have a bottom of predetermined width and side walls, and each of said sensor means comprise
a conductive substrate fastened to said recess bottom and having a width less than said predetermined width of said recess bottom;
interface means communicating with the conductive substrate for forming a conductive and galvanically inert interface between the conductive substrate and the patient's skin.

39. The apparatus of claim 38, wherein said interface means substantially fills the recess.

40. The apparatus of claim 33, wherein said sensor means comprise means for sensing ECG signals.

41. The apparatus of claim 40, wherein said ECG sensor means comprise:
a conductive substrate;
a thin layer of a conductive, galvanically inert substance enveloping said substrate; and
means affixed to said thin layer for forming a conductive and inert interface between said ECG sensor means and the patient's skin.

42. The apparatus of claim 41, wherein said interface forming means include a hydrogel.

43. The apparatus of claim 42, wherein said interface forming means include a striated surface.

44. The apparatus of claim 41, wherein said interface forming means include
a layer of carbonized rubber affixed to said thin layer.

45. The apparatus of claim 44, wherein said interface forming means include a striated surface having a diamond pattern.

46. The apparatus of claim 41, wherein said torso band means has a surface which comes in contact with the patient's skin, said surface further has recesses for housing said ECG sensor means, and said sensor means are adhesively attached bottom of said recesses and are generally flush with said surface.

47. The apparatus of claim 40, wherein said ECG sensor each comprise a layer of carbonized rubber.

48. The apparatus of claim 33, wherein said sensor means comprise means for sensing changes in the tension in said torso band means.

49. The apparatus of claim 48, wherein said means for sensing changes in tension comprise a strip of piezoelectric material positioned longitudinally in said torso band means.

50. The apparatus of claim 33, further including wiring means for providing electrical connection to said sensor means, said wiring means being formed in a manner which permits said wiring means to elongate when said torso band means are placed under tension.

51. The apparatus of claim 50, wherein said wiring means are embedded within a visco-elastic polymer located in said torso band means, and out of contact with the patient's skin.

52. The apparatus of claim 51, wherein said wiring means are snaked in an accordion fashion through the visco-elastic polymer to permit stretching of said torso band means.

53. The apparatus of claim 51, wherein said wiring means include a plurality of conductors which are woven together to form a structure that elongates when said torso band means elongate.

54. The apparatus of claim 50, wherein said wiring means are formed on a skin of said torso band means in a manner which permits said wiring means to elongate when said torso band means are placed under tension.

55. The apparatus of claim 33, further including a patient-activated switch positioned in the torso band means.

56. The apparatus of claim 55, wherein the switch is located in the center of the front portion of the torso band means.

57. The apparatus of claim 55, wherein the switch is located in said torso band means such that said switch is positioned under an arm of the patient.

* * * * *